United States Patent [19]

Igarashi et al.

[11] 4,273,923

[45] Jun. 16, 1981

[54] PROCESS FOR PREPARING AMINOGLYCOSIDE DERIVATIVES

[75] Inventors: Kikuo Igarashi, Itami; Tamio Sugawara, Mino, both of Japan

[73] Assignee: Shionogi & Co., Ltd., Osaka, Japan

[21] Appl. No.: 68,103

[22] Filed: Aug. 20, 1979

[51] Int. Cl.$^3$ .................. A61K 31/71; C07H 15/22
[52] U.S. Cl. .................................. 536/10; 424/180; 536/17 R
[58] Field of Search ............... 424/180; 536/17 R, 10

[56] References Cited

U.S. PATENT DOCUMENTS

| | | | |
|---|---|---|---|
| 4,001,209 | 1/1977 | Weinstein et al. | 536/17 R |
| 4,166,114 | 8/1979 | Igarashi | 536/17 R |
| 4,169,197 | 9/1979 | Magerlein | 536/17 R |

*Primary Examiner*—Johnnie R. Brown
*Attorney, Agent, or Firm*—Wenderoth, Lind & Ponack

[57] ABSTRACT

Novel aminoglycoside derivatives and their salts containing 2-deoxystreptamine moiety and 4',5'-unsaturation effective in treatment and prevention of infectious diseases caused by gram-positive and gram-negative bacteria.

3 Claims, No Drawings

PROCESS FOR PREPARING AMINOGLYCOSIDE DERIVATIVES

BACKGROUND OF THE INVENTION

Aminoglycoside antibiotics, for example, streptomycin, kanamycins, gentamicins, tobramycin, etc. have been used practically as broad spectrum antimicrobials effective against gram-positive, gram-negative and acid-fast bacteria. The aminoglycoside antibiotics, however, are sometimes accompanied by undesired side effect such as nephropathy and deafness. Occurrence of resistant strains against the aminoglycosides is another problem to be solved. Recently, it has been attempted to improve the antimicrobial activity and to relatively decrease the side effects by modification of such antibiotics. For instance, amikacin which is prepared by acylation of the 1-amino group of kanamycin A with (S)-4-amino-2-hydroxybutyric acid [Kawaguchi et al, J. Antibiotic 25, 695(1972); U.S. Pat. No. 3,781,268 (1973); J. Antibiotic 27, 677(1974)] is an excellent antimicrobial agent of which the activity is more potent than kanamycin A and of which the toxicity is approximately the same as kanamycin A.

SUMMARY OF THE INVENTION

This invention relates to novel aminoglycoside derivatives having excellent antimicrobial action.

The novel aminoglycoside antibiotic derivatives in this invention may be represented by the formula:

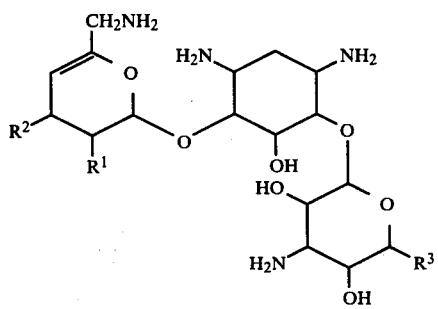

(wherein
$R^1$ is hydroxy or amino;
$R^2$ is hydrogen or hydroxy; and
$R^3$ is hydroxymethyl or carbamoyloxymethyl) and the salts thereof.

The novel aminoglycoside antibiotic derivatives (I) in this invention include the free bases and salts thereof, particularly non-toxic acid addition salts, for example, salts with inorganic acids such as hydrochloric acid, hydrobromic acid, hydroiodic acid, sulfuric acid, phosphoric acid, carbonic acid, and the like and salts with organic acids such as acetic acid, fumaric acid, malic acid, tartaric acid, maleic acid, citric acid, mandelic acid, ascorbic acid, gallic acid, and the like.

Representative of Compounds (I) is O-[3-amino-3-deoxy-α-D-glucopyranosyl-(1→6)]-O-[2,6-diamino-2,3,4,6-tetradeoxy-α-D-glycero-hex-4-enopyranosyl-(1→4)]-2-deoxy-D-streptamine.

PREPARATION

Compounds (I) of this invention may readily be prepared according to the following reaction Scheme:

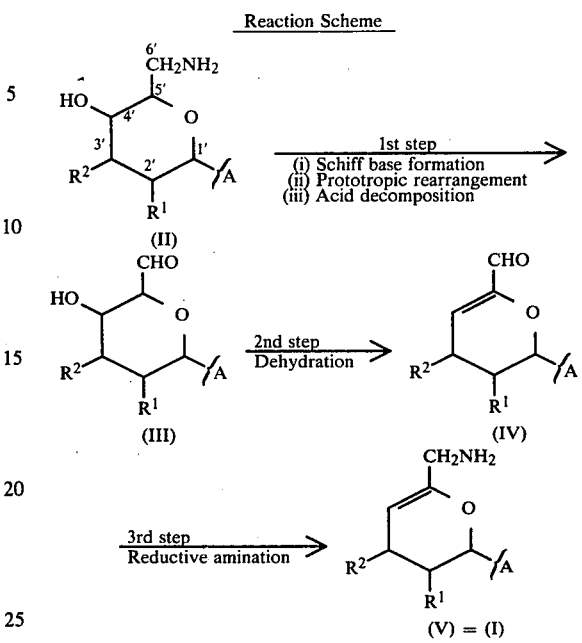

(wherein
$R^1$ and $R^2$ each has the same meaning as mentioned above; and
A represents the following partial formula:

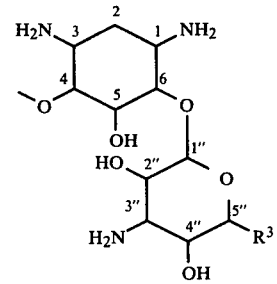

(wherein $R^3$ is hydroxymethyl or carbamoyloxymethyl.) In the above formula, those of which the functional groups are optionally protected, are also included within the definition of A.

The starting materials (II) are well-known aminoglycosides. Representative of the starting compounds (II) and their substituents are shown in Table 1.

TABLE 1

| Substituent Compound (II) | $R^1$ | $R^2$ | $R^3$ |
|---|---|---|---|
| tobramycin | NH₂ | H | CH₂OH |
| Kanamycin A | OH | OH | " |
| Kanamycin B | NH₂ | " | " |
| deoxykanamycin A | OH | H | " |
| nebramycin factor 4 | NH₂ | OH | CH₂OCONH₂ |
| nebramycin factor 5' | " | H | " |

The preparation of Compounds (I) is shown below.

(First Step)

The first step consists of formation of the Schiff base, prototropic rearrangement and subsequent acid decomposition. These three steps can be carried out successively.

(1) Formation of the Schiff base

This step may be carried out by reaction of the starting compound (II) with a carbonyl compound as described below in a suitable solvent. The reaction proceeds well at room temperature and is usually complete within 1 to 3 hours. If required, it is possible to accelerate the reaction by gentle heating. Preferably, the reaction is carried out under nitrogen atmosphere. The carbonyl compound to be employed may be selected from mesitylglyoxal, 3-nitromesitylglyoxal, and 3,5-dinitromesitylglyoxal. In carrying out this reaction, an equimolar or excess amount of the carbonyl compound, preferably 1 to 2 equivalents, may be used to one mole of the starting compound (II). Representative of the reaction solvents are alcohols such as methanol, ethanol and ethylene glycol, ethers such as diethyl ether, dioxane and tetrahydrofuran, dimethyl sulfoxide and the like, and they may be used alone or as a mixture of them.

Since the starting compounds (II) have many functional groups other than the 6'-amino group which readily react with carbonyl compounds, it is appropriate to optionally protect them by protecting groups preliminarily. Examples of the protecting groups include methoxycarbonyl, ethoxycarbonyl, trifluoroacetyl, and the like, and these protecting groups may be removed on treatment with an alkali after termination of the reaction.

(2) Prototropic Rearrangement

This step may be carried out by addition of a base to the above reaction medium. Representative of the bases are tertiary bases such as triethylamine, 1,5-diazabicyclo[5.4.0]undecene-5 (DBU), and 1,5-diazabicyclo[3.4.0]nonene-5 (DBN), alkali metal alcoholate such as sodium methoxide and sodium ethoxide and the like; the preferred base is DBN. This step may also be carried out at room temperature or under gentle heating in nitrogen atmosphere.

(3) Acid Decomposition

This step may be carried out by addition of an acid to the above reaction medium. The acids to be employed are weak acids, preferably carboxylic acids, for example, acetic acid, oxalic acid, pyruvic acid and the like. Preferably, the reaction is also carried out under nitrogen atmosphere, and is complete within 2 to 75 hours at room temperature. If required, it is possible to accelerate the reaction by warming. Additionally, if required, it is possible to shorten the reaction time by carrying out the reaction at pH 4.

(Second Step)

This step is achieved by addition of an acid to the above reaction product. As an acid, those employed in the acid decomposition of the above mentioned first step may be used. Alternatively, it is also appropriate to use acid anhydrides such as acetic anhydride, by which the reaction is completed more easily and the yield increased.

(Third Step)

This step may be achieved by reaction of Compound (IV) with an alcoholic ammonia or hydroxylamine to give the Schiff base or oxime, which is then reduced to the objective compound (V). The alcoholic ammonia means ammonia solutions saturated in alcohols such as methanol and ethanol. The reduction may be effected with metal hydrides such as lithium aluminium hydride and sodium borohydride.

Effects

The aminoglycoside derivatives and the non-toxic salts thereof prepared in this invention exhibit potent antimicrobial activities. They are several to several hundred times more active than the corresponding parent aminoglycosides against some species of gram-positive and gram-negative bacteria. Minimum Inhibitory Concentration (MIC, $\mu$g/ml) of the aminoglycoside of this invention and a standard tobramycin is indicated in Table 2.

MIC was determined by the following agar dilution method:

(1) Preparation of bacterial suspensions

One loopful of a strain of bacteria to be tested on agar slant was inoculated into a medium for growth of inoculum (Trypto Soy Broth; Eiken Chemical Co.) and incubated at 37° C. overnight.

(2) Preparation of medium for antibacterial activity test

A sample solution of aminoglycoside derivative was subjected to serial two-fold dilutions with sterile water. These diluted sample solutions were distributed to the Modified Mueller Hinton Agar medium (Nissui-Seiyaku Co.), mixed gently and allowed to solidify.

(3) Determination of MIC values

One loopful of the bacterial suspension prepared in (1) was placed on the surface of the medium prepared in (2) containing the aminoglycoside derivative in various concentrations at $10^6$ CFU/ml inoculum size. After incubating at 37° C. for 18 to 20 hours, the growth of bacteria on the medium was observed according to the standard method of Japan Society of Chemotherapy.

TABLE 2

| | MIC ($\mu$g/ml) innoculum size: $10^4$ CFU/ml | |
|---|---|---|
| | Compound | |
| Bacteria | [A] | TOB |
| *Staphylococcus epidermidis* TB-172* | 0.1 | 25.0 |
| *Staphylococcus epidermidis* TB-302 | 0.2 | 3.1 |
| *Escherichia coli* W-677/JR 762* | 12.5 | 50 |
| *Klebsiella pneumoniae* Kl-168* | 50.0 | 100 |
| *Proteus morganii* Morg. 96* | 12.5 | 25.0 |

[Note]

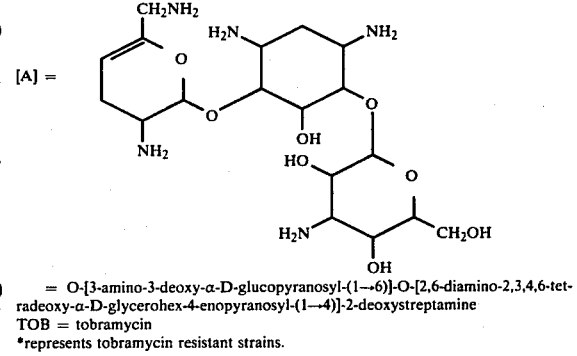

[A] = O-[3-amino-3-deoxy-α-D-glucopyranosyl-(1→6)]-O-[2,6-diamino-2,3,4,6-tetradeoxy-α-D-glycerohex-4-enopyranosyl-(1→4)]-2-deoxystreptamine
TOB = tobramycin
*represents tobramycin resistant strains.

As seen from Table 2, Compounds (I) of this invention have a potent antimicrobial action and are valuable as drugs for human or animal use. Accordingly, Compounds (I) of this invention may be used in treating or preventing various kinds of infectious diseases caused by the well-known aminoglycoside resistant bacteria, particularly *Staphylococcus epidermidis*, as well as those sensitive to the aminoglycoside antibiotics. Compounds (I) can also be used as disinfectants for preventing the growth of bacteria in perishables, feedstuffs, or hygenical materials.

How to use

Compounds (I) of this invention can be in a wide variety of oral or parenteral dosage forms solely or in admixture with other co-acting substances. The pharmaceutical compositions may be a mixture of 0.01 to 99% of Compounds (I) with a pharmaceutical carrier or carriers which can be a solid material or liquid material in which Compounds (I) are soluble, dispersible, or suspensible. They can be in a unit dosage form. The solid compositions can be in forms of tablets, powder, dry syrups, troches, granules, capsules, pills, suppositories, or like solid preparation. The liquid compositions can be in forms of injections, ointments, dispersions, inhalant, suspensions, solutions, emulsions, syrups, or elixirs. All of the diluents (e.g. starch, sucrose, lactose, calcium carbonate, kaolin); bulking agents (e.g. lactose, sugar, salt, glycine, starch, calcium carbonate, calcium phosphate, kaolin, bentonite, talc, sorbitol); binders (e.g. starch, acacia, gelatin, glucose, sodium arginate, tragacanth, carboxymethylcellulose, sorbitol, polyvinylpyrrolidone); disintegrators (e.g. starch, agar, carbonates, sodium laurylsulfate), lubricant (e.g. stearic acid, talc, paraffin, boric acid, silica, sodium benzoate, polyethylene glycol, cacao oil, magnesium sulfate); emulsifying agents (e.g. lecithin, sorbitan monooleate, acacia); suspending agents (e.g. sorbitol, methylcellulose, glucose, sugar syrup, gelatin, hydroxyethylcellulose, carboxymethylcellulose, aluminum stearate gel, hydrogenated fats); solvents (e.g. water, peanut oil, sesame oil, methyl oleate); preservatives (e.g. methyl or ethyl p-hydroxybenzoate, sorbic acid), edible coloring agents, aromatic substances, solubilizing agents, buffers, stabilizing agents, dispersing agents, wetting agents, antioxidants, and the like can be used in the conventional manner as far as they do not act adversely on Compounds (I).

Compounds (I) of this invention, particularly, their sulfates, are readily soluble in water and conveniently used as solutions for intravenous, intramusclar, or subcutaneous injections according to a conventional method. Compounds (I) can be dissolved in an ampoule or oily solvent for injection to give an injectable solution in ampoule; in order to preserve the injectable preparation for a long period of time, it is appropriate to make a vial preparation containing crystals, powder, microcrystals, or lyophilizate of Compounds (I). The vial preparation may be dissolved or suspended in the said solvents for injection immediately before use. The preparation may contain said preservatives.

Further, Compounds (I) of this invention can be used as suppositories, ointments for topical or opthalmic use, powders for topical use, and like preparations preparable according to the methods well-known to those skilled in the art. The external preparation can contain 0.01 to 99% of Compounds (I) of this invention together with a necessary amount of pharmaceutical carrier given above.

This invention also provides a method for treating or preventing infections caused by bacteria in humans or domestic animals, which comprises administering to the humans or animals Compounds (I) of this invention at a divided or single dose of 0.01 to 5 g/kg a day for injection, 0.01 to 10 g/kg a day for oral administration, or 0.01 to 10 g a day for topical application at intervals of 3 to 12 hours.

The method is applicable for treating or preventing some infectious diseases caused by bacteria sensitive to the compounds of this invention, e.g. staphylodermia, anthropozoonosis, cystitis, pyelitis, pneumonia, pneumonitis, bronchitis, empyematic, naspharyngitis, tonsilitis, rhinitis, dermatitis, pustulosis, abscess, wound and soft tissue infections, ear infections, osteomyelitis, septicemia, enteritis, urinary tract infections, and pyelonephritis.

Preferably, Compounds (I) of this invention are given to a patient in forms of pharmaceutical preparation, e.g. powder, dry syrup, tablets, troches, granules, capsules, pills, suppositories, injections, ointments, dispersions, inhalant, suspensions, solutions, emulsions, syrups and elixirs. They may be in a unit dosage form e.g. tablets, troches, capsules, injections, vials, granules or powder in a separate container of package.

The following examples are provided or further illustrate this invention.

EXAMPLE A (1) 1,3,2',3''-Tetra-N-ethoxycarbonyltobramycin [Belgian Pat. No. 836,127] (7 g; 9.26 mmoles) is dissolved in 35 ml of dimethylsulfoxide and the mixture is stirred at room temperature under nitrogen atmosphere for 2 hours. DBN (115 mg; 0.1 molar equivalent) is added thereto and the mixture is stirred at room temperature under nitrogen atmosphere for 24 hours. Then, 21 ml of methanol and 2.33 g (2 molar equivalents) of oxalic acid dihydrate are added thereto. The mixture is stirred at room temperature under nitrogen atmosphere for 72 hours, then diluted with 350 ml of water and filtered. The filtrate is slowly passed through a column of Amberlite MB-3 (140 ml), and the column is washed with 150 ml of water. The combined eluate and washing are evaporated to dryness under reduced pressure. The residue is dissolved in a small amount of methanol and treated with 10 parts by volume of ether. The resulting precipitate is collected by filtration and washed with ether to give 1.16 g of a crude mixture of the saturated aldehyde and the unsaturated aldehyde in 17% yield.

(2) A solution of 1.08 g of the above crude product in 50 ml of 9 (w/w)% methanol saturated with ammonia is stirred at room temperature for 1 hour. Sodium borohydride (750 mg) is added thereto, and the mixture is stirred at room temperature for 1 hour and evaporated to dryness under reduced pressure. The resulting residue is chromatographed on a column of Kiesel gel 60 (38 g) and eluted with a mixture of isopropanol—ammonium hydroxide—chloroform (4:1:1) (each fraction: 5 ml). Fraction Nos. 7 to 19 are collected and the solvent is distilled off. The residue (1.19 g) is rechromatographed on a column of Kiesel gel 60 (80 g) and eluted with a mixture of isopropanol—ammonium hydroxide—chloroform (10:1:1) (each fraction: 5 ml). Fraction Nos. 22 to 26 are collected and the solvent is evaporated to give 249 mg of residue.

(3) A solution of 249 mg of the above residue in 20 ml of water containing 1.5 g of barium hydroxide octahydrate is stirred under heating at 105° C. for 16 hours. After cooling, the solution is adjusted at pH 6 with diluted sulfuric acid and filtered. The filtrate is evaporated to dryness under reduced pressure. The residue (210 mg) is chromatographed on a column of 100 ml of Amberlite CG-50 (NH$_4^+$ type) and eluted with 1 L of water and 1 L of 1 N aqueous ammonium hydroxide solution by a gradient method (each fraction: 12 ml). Fraction Nos. 68 to 76 are collected and concentrated under reduced pressure. The resulting residue (60 mg) is chromatographed on a column of Kiesel gel 60 (60 g) and eluted with a lower layer of chloroform—methanol—ammonium hydroxide solution (1:1:1) (each fraction: 8 ml). Fraction Nos. 45 to 63 are collected and the solvent is evaporated. The resulting residue is dissolved in a small amount of water and purified by means of chromatography using 10 ml of Amberlite CG-50 ($NH_4^+$ type) and 50 ml of 1 N aqueous ammonium hydroxide solution as an eluent. The eluate is concentrated under reduced pressure to give 23 mg of O-[3-amino-3-deoxy-α-D-glucopyranosyl-(1→6)]-O-[2,6-diamino-2,3,4,6-tetradeoxy-α-D-glycero-hexa-4-enopyranosyl-(1→4)]-2-deoxy-streptamine in 0.55% yield.

(4) A solution of the above product in 3 ml of water is adjusted at pH 6 with 0.099 N sulfuric acid, concentrated to 1 ml under reduced pressure, and treated with 30 ml of ethanol. The resulting precipitate is collected by filtration, washed with ethanol, dissolved in water, treated with active carbon and lyophilized. The lyophilizate is allowed to stand until the weight becomes constant by absorption of moisture. Thus, 27 mg of the sulfate of the product prepared in the above (3) is produced.

$[\alpha]_D^{26} + 91.9 \pm 6.2°$ (c=0.210, $H_2O$)

Elemental Analysis (for $C_{18}H_{35}N_5O_8 \cdot 2.3H_2SO_4 \cdot 10-H_2O$)

Calcd(%): C, 25.27; H, 7.02; N, 8.19; S, 8.62.
Found(%): C, 25.07; H, 7.13; N, 8.31; S, 8.70.

NMR: $\delta_{ppm}^{D2O}$ 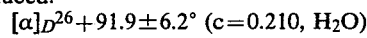 5.45–5.81(m,2H), 6.10(s,1H)

EXAMPLE B (1) 1,3,2',3''-Tetra-N-ethoxycarbonyltobramycin (2.5 g; 3.308 mmoles) is dissolved in 12.5 ml of dimethylsulfoxide, and the mixture is stirred at room temperature for 2 hours. DBN (41 mg; 0.1 molar equivalent) is added thereto, and the mixture is stirred at room temperature under nitrogen atmosphere for 24 hours and concentrated under reduced pressure. The residue is dissolved in a small amount of methanol and treated with 10 parts by volume of ether. The resulting precipitate is collected by filtration and washed with ether to give 1.8 g of the product in 60.6% yield.

(2) A mixture of 3 ml of acetic acid, 2 ml of water and 50 (w/w)% aqueous solution of 0.7 g of pyruvic acid is adjusted at pH 4.1 with sodium acetate. To 1 ml of the above adjusted solution is added 100 mg of the product prepared in the above (1), and the reaction mixture is stirred at room temperature under nitrogen atmosphere for 2.5 hours and concentrated under reduced pressure. The residue is dissolved in 20 ml of an aqueous methanol and passed through a column of 20 ml of Amberlite MB-3. The column is washed with 30 ml of an aqueous methanol. The combined eluate and washing are concentrated under reduced pressure to give 50 ml of the saturated aldehyde compound in 59.5% yield.

(3) To a solution of 50 mg of the above product in 1 ml of pyridine is added 0.15 ml of acetic anhydride, and the mixture is stirred at 50° C. under nitrogen atmosphere for 20 hours, and concentrated under reduced pressure to give 60 mg of the unsaturated aldehyde compound.

(4) A solution of 60 mg of the above product dissolved in 2.5 ml of 9(w/w)% methanol saturated with ammonia is stirred at room temperature for 5 hours. Sodium borohydride (5 mg) is added thereto, and the mixture is stirred at room temperature for 30 minutes and concentrated under reduced pressure. The resulting residue is chromatographed on a column of 40 g of Kiesel gel 60 and eluted with isopropanol—ammonium hydroxide—chloroform (10:1:1) (each fraction: 5 ml). Fraction Nos. 28 to 39 are collected and evaporated under reduced pressure. The resulting residue is dissolved in 25 ml of an aqueous solution of barium hydroxide octahydrate, and the solution is stirred at 105° C. for 16 hours. After cooling, the solution is adjusted at pH 6 with diluted sulfuric acid and filtered. The filtrate is concentrated under reduced pressure, and the residue is adsorbed on a column of 20 ml of Amberlite CG-50 ($NH_4^+$ type) and eluted with 1 L of water and 1 L of 1 N aqueous ammonium hydroxide solution by a gradient method (each fraction: 12 ml). Fraction Nos. 35 to 40 are concentrated under reduced pressure to give 9 mg of O-[3-amino-3-deoxy-α-D-glucopyranosyl-(1→6)]-O-[2,6-diamino-2,3,4,6-tetradeoxy-α-D-glycero-hexa-4-enopyranosyl-(1→4)]-2-deoxy-streptamine in 5.6% yield.

We claim:

1. A process for preparing a compound of the formula:

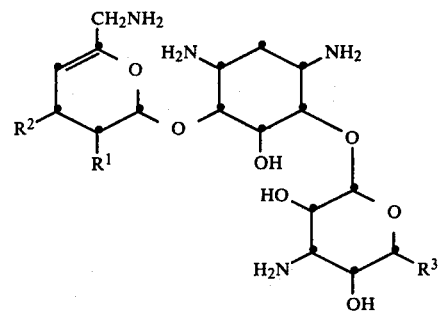

wherein
$R^1$ is hydroxy or amino;
$R^2$ is hydrogen or hydroxy; and
$R^3$ is hydroxymethyl or carbamoyloxymethyl
which comprises reacting an aminoglycoside of the formula:

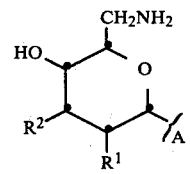

wherein A represents a group of the formula:

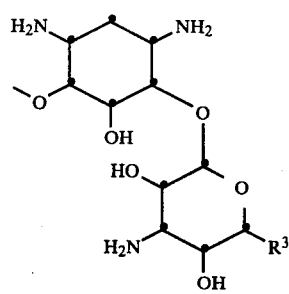

and in which the amino groups other than the 6'-amino group are preliminarily protected with ethoxycarbonyl group with a carbonyl compound selected from the group consisting of mesitylglyoxal, 3-nitromesitylglyoxal, and 3,5-dinitromesitylglyoxal to give the corresponding Schiff base, subjecting the latter to prototropic rearrangement on treatment with a base selected from the group consisting of triethylamine, 1,5-diazabicyclo[5.4.0]undecene-5, 1,5-diazabicyclo[3.4.0]nonene-5, sodium methoxide, and sodium ethoxide, and subsequent acid decomposition with an acid selected from the group consisting of acetic acid, oxalic acid, and pyruvic acid to give a compound of the formula:

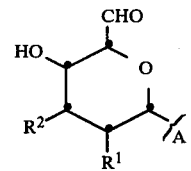

subjecting the latter to dehydration with an acid selected from the group consisting of acetic acid, oxalic acid, and pyruvic acid to give a compound of the formula:

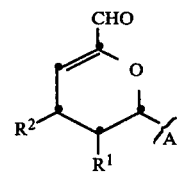

and subjecting the latter to reductive amination by reaction with an alcoholic ammonia or hydroxylamine and a metal hydride and to deprotection by hydrolysis.

2. A process as claimed in claim 1, wherein the carbonyl compound is mesitylglyoxal.

3. A process as claimed in claim 1, wherein prototropic rearrangement is effected with 1,5-diazabicyclo[3.4.0]nonene-5.

* * * * *

UNITED STATES PATENT AND TRADEMARK OFFICE
CERTIFICATE OF CORRECTION

PATENT NO. : 4,273,923
DATED : June 16, 1981
INVENTOR(S) : KIKUO IGARASHI and TAMIO SUGAWARA It is certified that error appears in the above-identified patent and that said Letters Patent are hereby corrected as shown below:

On page 1 of the patent document (the cover sheet), immediately following the section reading "[22] Filed: August 20, 1979" insert the following:

-- [30] Foreign Application Priority Data
September 14, 1978 [JP] Japan 53-113404 --

Signed and Sealed this

Third Day of August 1982

[SEAL]

Attest:

GERALD J. MOSSINGHOFF

Attesting Officer    Commissioner of Patents and Trademarks